(12) United States Patent
Moon et al.

(10) Patent No.: US 8,150,318 B2
(45) Date of Patent: Apr. 3, 2012

(54) APPARATUS FOR COLLECTING ENVIRONMENTAL DATA AND METHOD OF MONITORING ENVIRONMENT IN REAL TIME

(75) Inventors: Seung Eon Moon, Daejeon (KR); Eun Kyoung Kim, Daejeon (KR); Hong Yeol Lee, Chungcheongbuk-do (KR); Jong Hyurk Park, Daegu (KR); Kang Ho Park, Daejeon (KR); Jong Dae Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 851 days.

(21) Appl. No.: 12/195,176

(22) Filed: Aug. 20, 2008

(65) Prior Publication Data

US 2009/0061772 A1  Mar. 5, 2009

(30) Foreign Application Priority Data

Sep. 4, 2007 (KR) .................. 10-2007-0089596

(51) Int. Cl.
*H04B 7/00* (2006.01)

(52) U.S. Cl. .................. 455/41.2; 455/3.06; 455/414.3; 455/414.4; 455/575.2; 455/563; 340/825.25; 379/908

(58) Field of Classification Search ............... 455/41.2, 455/563, 569.1, 556.1, 575.2, 414.1, 3.06, 455/414.3, 414.4; 340/573.2, 5.1
See application file for complete search history.

(56) References Cited

U.S. PATENT DOCUMENTS

| | | | |
|---|---|---|---|
| 7,027,808 B2* | 4/2006 | Wesby | 455/419 |
| 7,289,825 B2* | 10/2007 | Fors et al. | 455/556.1 |
| 7,778,601 B2* | 8/2010 | Seshadri et al. | 455/41.2 |
| 7,905,815 B2* | 3/2011 | Ellis et al. | 482/8 |
| 2003/0095525 A1* | 5/2003 | Lavin et al. | 370/338 |
| 2006/0251277 A1* | 11/2006 | Cho | 381/311 |
| 2008/0305779 A1* | 12/2008 | Wright et al. | 455/414.1 |

FOREIGN PATENT DOCUMENTS

| | | |
|---|---|---|
| KR | 1020060028324 A | 3/2006 |
| KR | 10-2006-0061465 A | 6/2006 |
| KR | 10-2006-0112725 A | 11/2006 |

\* cited by examiner

*Primary Examiner* — Marceau Milord

(57) ABSTRACT

Provided are an apparatus for collecting environmental data and a method of monitoring an environment in real time. The apparatus for collecting environmental data includes a receiver for receiving an environmental data collection command from outside, a headset controller for interpreting the environmental data collection command received from the receiver, and distinguishing an audio signal received from outside from the environmental data collection command, the environment sensor unit for collecting environmental data according to the environmental data collection command interpreted from the headset controller, and a transmitter for transmitting the environmental data collected by the environment sensor unit.

9 Claims, 3 Drawing Sheets

APPARATUS FOR COLLECTING ENVIRONMENTAL DATA AND METHOD OF MONITORING ENVIRONMENT IN REAL TIME

CROSS-REFERENCE TO RELATED APPLICATION

This application claims priority to and the benefit of Korean Patent Application No. 2007-89596, filed Sep. 4, 2007, the disclosure of which is incorporated herein by reference in its entirety.

BACKGROUND

1. Field of the Invention

The present invention relates to an apparatus for collecting environmental data and a method of monitoring an environment in real time.

This work was supported by the IT R&D program of MIC/IITA [2006-S-006-02. Components/Module technology for Ubiquitous Terminals].

2. Discussion of Related Art

By connecting a computer with a peripheral device, a mobile communication terminal with a computer, household appliances, etc., within a short range via a wireless network, short-range wireless communication enables bidirectional real-time communication without electric cables. Lately, Bluetooth has been adopted as a short-range wireless communication standard, and modules implementing Bluetooth are being produced in the form of a chip. Bluetooth is wireless data communication technology developed by a consortium of Ericsson, Nokia, Intel, IBM and Toshiba, which are mobile communication service providers and computer companies, in 1998 to solve a problem that too many connection cables are required for a connection between mobile devices. Bluetooth has been developed to replace cables on the basis of low cost, low power consumption and a wireless environment.

A Bluetooth headset is a typical wireless communication device employing Bluetooth technology. The Bluetooth headset is not connected with a mobile communication terminal through an electric cable, and enables bidirectional data communication using short-range wireless communication. A telephony method using such a Bluetooth headset is the same as a generally-used hands-free scheme that does not require an electric cable.

Meanwhile, according to a conventional environment monitoring method, a sensor is separated from a controller and a processor. Since the respective sub-systems are very big and consume much power, they are spaced far apart from each other or connected through a cable. Therefore, it is difficult to timely and spatially satisfy a user's demands for health information and real-time environmental information on abnormal weather. Consequently, a portable apparatus for providing specific environmental information to a user is required.

SUMMARY OF THE INVENTION

The present invention is directed to providing an apparatus for collecting environmental data and a method of monitoring an environment in real time using the apparatus.

The present invention is also directed to proposing an apparatus for collecting environmental data capable of readily measuring an environmental state of any place that a user wants without a restriction on location, and a method of monitoring an environment in real time using the apparatus.

One aspect of the present invention provides an apparatus for collecting environmental data, including: a receiver for receiving an environmental data collection command from outside; a headset controller for interpreting the environmental data collection command received from the receiver, and distinguishing an audio signal received from outside from the environmental data collection command; the environment sensor unit for collecting environmental data according to the environmental data collection command interpreted from the headset controller; and a transmitter for transmitting the environmental data collected by the environment sensor unit.

The environmental data collection command received by the receiver and the environmental data transmitted from the transmitter may be transmitted using Bluetooth. The environment sensor unit may collect at least one of a degree of surrounding noise, a discomfort index, a concentration of fine particles, a concentration of harmful gas, temperature and humidity. The apparatus may further include: a sound receiver for receiving the audio signal from outside; and a sound processor for outputting the received audio signal through an external speaker. The environmental data collection command and the audio signal may be received from a mobile communication terminal.

The apparatus may further include a portable terminal for transmitting the environmental data collection command, receiving the collected environmental data, and displaying the received environmental data in comparison with previously stored local environmental data according to a type of the environmental data. The apparatus may function as a headset of a portable mobile terminal.

Another aspect of the present invention provides a method of monitoring an environment in real time, including: receiving a signal from a portable terminal; determining whether the received signal is an environmental data collection command signal or a general audio signal, and requesting an environment sensor unit to collect environmental data when the received signal is an environmental data collection command signal; receiving an environmental data signal from the environment sensor unit; and transmitting surrounding environmental data included in the received environmental data signal to the portable terminal. Here, the portable terminal receiving a signal including the surrounding environmental data displays the surrounding environmental data in comparison with previously stored local environmental data according to a type of the surrounding environmental data.

The previously stored local environmental data may be environmental data collected according to regions by an existing environmental data collection institution. The environment data may include at least one of a degree of surrounding noise, a discomfort index, a concentration of fine particles, a concentration of harmful gas, temperature and humidity. When data included in the received signal is audio data, the received audio data may be output through a speaker.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Figure 1:
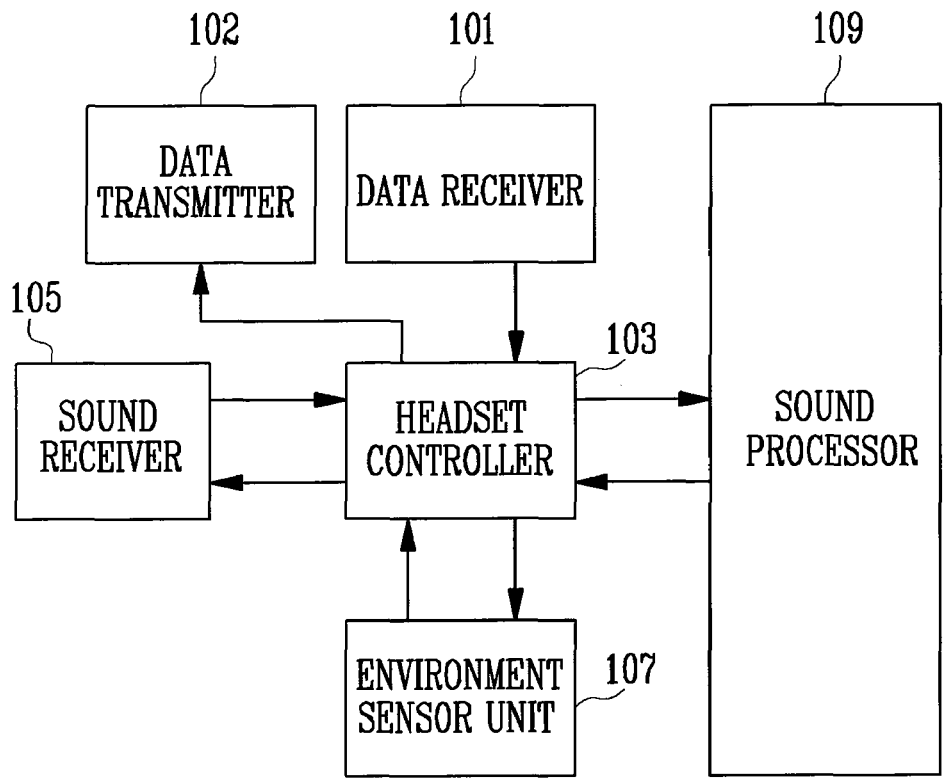
FIG. 1 is a block diagram of a headset capable of collecting environmental data according to an exemplary embodiment of the present invention.

FIG. 1 is a block diagram of a headset capable of collecting environmental data according to an exemplary embodiment of the present invention.

Referring to FIG. 1, the headset according to an exemplary embodiment of the present invention includes a data receiver 101, a data transmitter 102, a headset controller 103, a sound receiver 105, an environment sensor unit 107 and a sound processor 109.

The data receiver 101 functions to receive an environmental data collection command signal transmitted from a portable terminal, and the data transmitter 102 functions to transmit an environmental data signal. The data receiver 101 and the data transmitter 102 can transmit and receive a command through wireless communication. In particular, since the portable mobile communication terminal is not far from the headset, Bluetooth may be used.

The headset controller 103 functions to receive the environmental data collection command signal transferred from the data receiver 101 and an audio signal transferred from the sound receiver 105, interpret the respective signals, and transfer the audio signal to the sound processor 109 and the environmental data collection command signal to the environment sensor unit 107.

The sound receiver 105 functions to receive a general audio signal from the portable mobile communication terminal. Like a conventional headset, the sound receiver 105 may be wired or wirelessly connected with the portable mobile communication terminal. In the case of wireless communication, the sound receiver 105 may receive an audio signal using Bluetooth.

The environment sensor unit 107 functions to perform analog-digital conversion on the environmental data collection command signal and actually collect data of an environment around the headset using an environment sensor. Various pieces of environmental data may be collected according to the type of the environment sensor included in the headset, and the environment data may include a degree of surrounding noise, a discomfort index, a concentration of fine particles, a concentration of harmful gas, temperature, humidity, and so on.

The sound processor 109 functions to process the audio signal received from the headset controller 103, convert the input audio signal into a sound that can listen to a speaker and so on, and output the sound.

Figure 2:
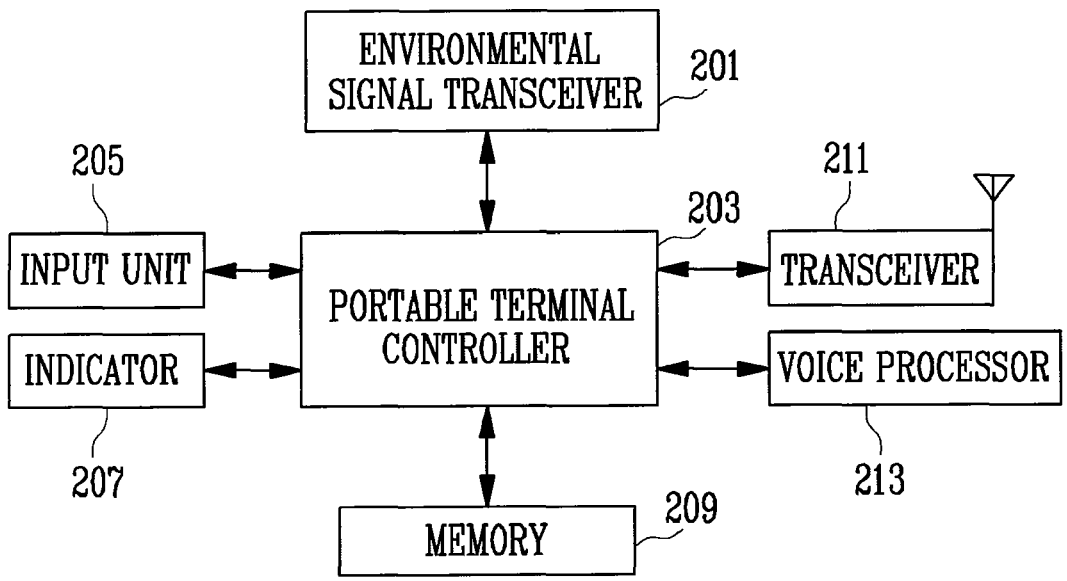
FIG. 2 is a block diagram of a portable terminal according to an exemplary embodiment of the present invention.

FIG. 2 is a block diagram of a portable terminal according to an exemplary embodiment of the present invention.

Referring to FIG. 2, the portable terminal according to an exemplary embodiment of the present invention includes an environmental signal transceiver 201, a portable terminal controller 203, an input unit 205, an indicator 207, a memory 209, a voice processor 213 and a transceiver 211.

The portable terminal controller 203 receives a signal processed by the transceiver 211 and controls the entire operations of the portable terminal. In addition, the portable terminal controller 203 functions to receive an environmental data collection command from the input unit 205, transfer the command to the environmental signal transceiver 201, and transfer a collected environmental data received from the environmental signal transceiver 201 to the indicator 207. In particular, the portable terminal controller 203 may analyze actually collected environmental data in comparison with existing local environmental data previously stored in the memory 209, and transfer data that a user wants to the indicator 207. Here, the local environmental data denotes environmental data that has been previously collected according to specific regions. Through the comparison, it is possible to know a difference between the environment of a current location and the average environment of a region.

The indicator 207, which may be a Liquid Crystal Display (LCD), a vibrator, a speaker, etc., is controlled by the controller 203 to indicate a state of the portable terminal and the progression of a program. In other words, the indicator 207 indicates an overall state of the portable terminal and input user information, and so on.

The memory 209 stores an operating program and a system program of the controller 203. The operating program or the system program may be stored in a generally included Read-Only Memory (ROM) and removed according to needs. As an electrically erasable memory, there is an Electrically Erasable Programmable ROM (EEPROM), a flash memory, and so on. In particular, the memory 209 may store existing local environmental data received from outside.

The voice processor 213 functions to modulate a voice signal input from a microphone into voice data, demodulate voice data input from the transceiver 211 and voice data stored in the memory 209 into a voice signal and output the voice signal.

The transceiver 211 is controlled by the controller 203, and functions to convert a receiving signal from the controller 203 into a wireless signal, and functions to convert a wireless signal received through an antenna into a desired signal.

Finally, the environmental signal transceiver 201 functions to receive an environmental data collection command signal from the portable terminal controller 203, transmit the environmental data collection command signal to outside, receive a result of transmission and transfer the result to the portable terminal controller 203. The environmental signal transceiver 201 can perform wireless communication with a device for collecting environmental data, and in particular, can transmit and receive a signal using Bluetooth, which is widely used as a short-range wireless communication standard.

Figure 3:
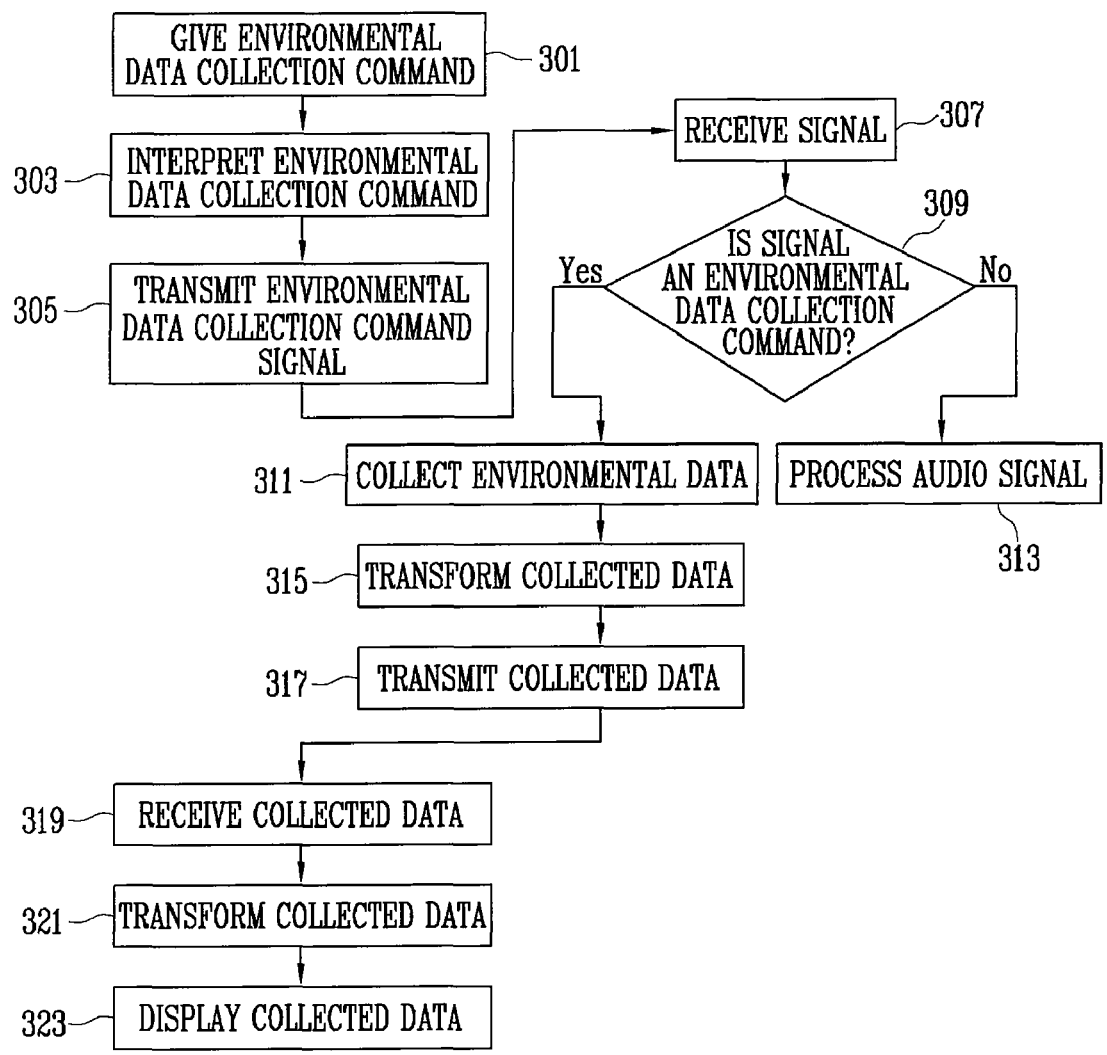
FIG. 3 is a flowchart showing a process of collecting environmental data and monitoring an environment according to an exemplary embodiment of the present invention.

FIG. 3 is a flowchart showing a process of collecting environmental data and monitoring an environment according to an exemplary embodiment of the present invention.

Referring to FIG. 3, a user gives an environmental data collection command by manipulating a specific key or using a specific command to a portable terminal (step 301). The portable terminal receiving the environmental data collection command interprets the command, transforms an environmental data collection command signal into a transmittable form and adds necessary data to the signal (step 303). For example, when the environmental data collection command is transmitted in a Bluetooth environment, the command signal is transformed into a form corresponding to the Bluetooth environment, which is the above-mentioned transmittable form. As an additional example, when a general audio signal and the environmental data collection command of the portable terminal use Bluetooth devices having the same channel, a header or tag indicating that a signal is an environmental data collection command signal, which is the above-mentioned necessary data, is added to the signal.

Subsequently, the interpreted environmental data collection command is transmitted to a headset including an environmental data collection device (step 305). The command may be transferred wired or wirelessly, but may be wirelessly transmitted to freely position an environment sensor included in the environmental data collection device and efficiently collect environmental data. In particular, Bluetooth, which is generally used in portable mobile communication terminals to transmit an audio signal, may be used to transmit the command.

Then, the headset receives the environmental data collection command from the portable terminal (step 307). The headset is a general headset of a portable terminal to which an environment sensor and a controller for collecting environmental data are added, and may have a similar size and shape to a general portable terminal headset.

Subsequently, it is determined whether a signal received from a headset controller is an environmental data collection command signal (step 309). A signal transmitted from a mobile communication terminal may be an environmental data collection command or a general audio signal. Thus, the received signal is interpreted, and it is determined which signal the received signal is.

When the received signal is an environmental data collection command signal, the received environmental data collection command is interpreted, and the environment sensor included in the headset is controlled to collect environmental data (step 311). Environmental data collected by the environment sensor may vary according to a characteristic of the environment sensor. The environment sensor can accurately recognize an environment around the headset and thus can collect data of an environment most near a user. The environment sensor may collect a degree of surrounding noise, a discomfort index, a concentration of fine particles, a concentration of harmful gas, temperature, humidity, etc., according to a characteristic thereof.

Subsequently, the collected environmental data is transformed into an appropriate format (step 315), and the collected environmental data is transmitted to the terminal receiving the environmental data collection command (step 317). Transfer of the data may be performed in a wireless environment, and in particular, the signal may be transmitted using Bluetooth. An environmental data signal transmitted from the headset is received by the portable terminal (step 319), and the received signal is transformed into an appropriate format by a portable terminal controller (step 321). Here, the portable terminal controller may analyze the received signal in comparison with previously received and stored local environmental data, and transform the received signal into an appropriate format for a user to understand.

Then, environmental information requested by the user is output through an audio device or display according to a format (step 323).

When data is collected in this method, a user can accurately check information on an environment around a headset in real time, i.e., rapidly, through a portable terminal.

Figure 4:
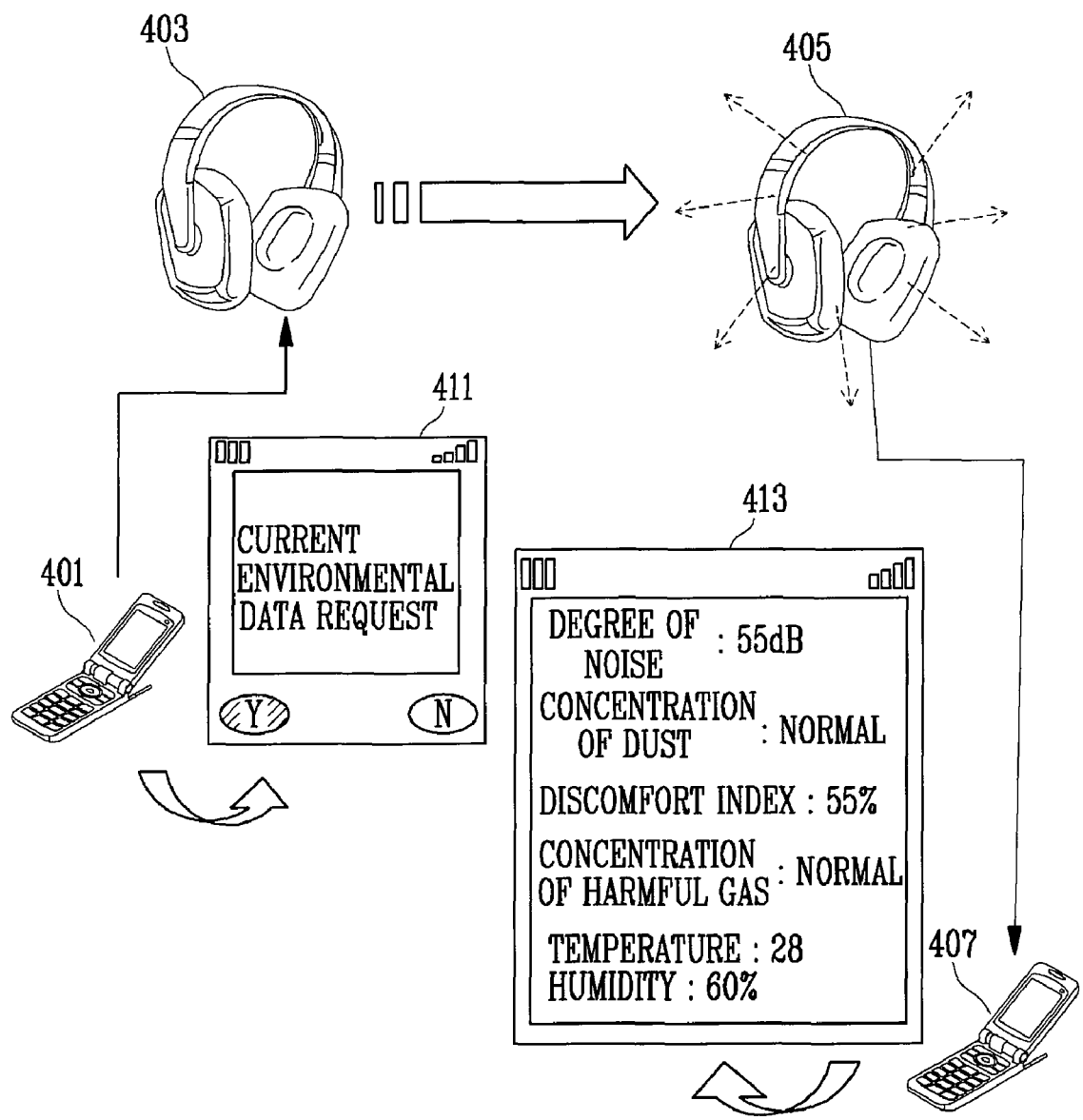
FIG. 4 shows an example of environmental information shown according to an exemplary embodiment of the present invention.

FIG. 4 shows an example of environmental information shown according to an exemplary embodiment of the present invention.

Referring to FIG. 4, a user transmits a current environmental information request 411 through his/her portable terminal 401. The portable terminal 401 transmitting the current environmental data request can give an environmental data request command and also perform the function of a general cellular phone. In addition, the portable terminal 401 may transmit a current environmental data request command signal through software manipulation only. In this case, the portable terminal 401 may have a short-range wireless communication function, such as a Bluetooth function, of transmitting an environmental data signal.

When current environmental data is requested through the portable terminal as described above, the environmental data request signal is transmitted to a headset 403 connected with the portable terminal 401. The environmental data request signal may be transmitted in any format, but in general, may be transmitted using Bluetooth, which is a short-range wireless communication standard, such that an environment sensor can be used without a restriction on location.

A headset 405 receiving the environmental data request 411 operates a sensor built in the headset 405 to collect information on an environment around the headset 405. In this case, since the headset 405 is put on a user's head, data of an environment that the user can directly see and feel is collected. Therefore, it is possible to collect environmental data as suited to the user himself/herself as incomparable to conventionally collected environmental data.

The collected environmental data that is suited to the user is transmitted again to a portable terminal 407, and the portable terminal 407 interprets and transforms the received data into appropriate information 413 for the user and displays the information 413. The displayed information 413 may be information transformed into a format that the user wants and can readily understand as a difference obtained by analyzing the data received by the portable terminal 407 from the headset 405 in comparison with previously received local environmental data.

Environmental information shown in FIG. 4 is an example, and thus a method of indicating information and a content of the environmental information according to the present invention are not necessarily the same as or similar to those of FIG. 4. According to needs or the type of the environment sensor included in the headset, it is possible to check user's temperature, pulse, etc., as well as surrounding environmental information. In addition, several pieces of other personal information can be provided.

According to the present invention, it is possible to provide an apparatus for collecting environmental data and a method of monitoring an environment in real time using the apparatus.

In addition, it is possible to provide an apparatus for collecting environmental data capable of readily measuring an environmental state of any place that a user wants without a restriction on location, and a method of monitoring an environment in real time using the apparatus.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An apparatus for collecting environmental data, comprising:
   a portable terminal;
   a receiver configured to receive an environmental data collection command from the portable terminal;
   a headset controller configured to interpret the environmental data collection command received from the portable terminal, and distinguish an audio signal received from the portable terminal from the environmental data collection command;

an environment sensor unit configured to collect environmental data according to the environmental data collection command interpreted from the headset controller; and
a transmitter configured to transmit the environmental data collected by the environment sensor unit to the portable terminal,
wherein the portable terminal is configured to transmit the environmental data collection command, receive the collected environmental data, and display the received environmental data in comparison with previously stored local environmental data according to a type of the environmental data.

2. The apparatus of claim 1, wherein the environmental data collection command received by the receiver and the environmental data transmitted from the transmitter are transmitted using Bluetooth.

3. The apparatus of claim 1, wherein the environment sensor unit collects at least one of a degree of surrounding noise, a discomfort index, a concentration of fine particles, a concentration of harmful gas, temperature and humidity.

4. The apparatus of claim 1, further comprising:
a sound receiver configured to receive the audio signal from the portable terminal; and
a sound processor configured to output the received audio signal through an external speaker.

5. The apparatus of claim 1, wherein the apparatus functions as a headset of the portable terminal.

6. A method of monitoring an environment in real time, comprising:
receiving a signal from a portable terminal;
determining whether the received signal is an environmental data collection command signal or an audio signal, and requesting an environment sensor unit to collect environmental data when the received signal is an environmental data collection command signal;
receiving an environmental data signal from the environment sensor unit;
transmitting the collected environmental data included in the received environmental data signal to the portable terminal; and
displaying the collected environmental data in comparison with previously stored local environmental data according to a type of the collected environmental data.

7. The method of claim 6, wherein the previously stored local environmental data is environmental data collected according to regions by an existing environmental data collection institution.

8. The method of claim 6, wherein the environmental data includes at least one of a degree of surrounding noise, a discomfort index, a concentration of fine particles, a concentration of harmful gas, temperature and humidity.

9. The method of claim 6, wherein when data included in the received signal is audio data, the received audio data is output through a speaker.

* * * * *